United States Patent
Ohtake et al.

(10) Patent No.: US 7,180,056 B2
(45) Date of Patent: Feb. 20, 2007

(54) MASS SPECTROMETRY AND MASS SPECTROMETRY SYSTEM

(75) Inventors: Atsushi Ohtake, Hitachiota (JP); Kinya Kobayashi, Hitachi (JP); Kiyomi Yoshinari, Hitachi (JP); Toshiyuki Yokosuka, Hitachi (JP); Atsumu Hirabayashi, Kodaira (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/143,717

(22) Filed: Jun. 3, 2005

(65) Prior Publication Data

US 2005/0274884 A1    Dec. 15, 2005

(30) Foreign Application Priority Data

Jun. 4, 2004    (JP) ............................. 2004-166728

(51) Int. Cl.
  *H01J 49/00*    (2006.01)
  *C12P 19/34*    (2006.01)
  *G01N 33/53*    (2006.01)
(52) U.S. Cl. ..................... 250/282; 250/286; 250/288; 530/350; 435/6; 436/56; 436/174
(58) Field of Classification Search ............... 250/281, 250/282, 286–288, 292, 294, 299
See application file for complete search history.

(56) References Cited

U.S. PATENT DOCUMENTS

| | | | |
|---|---|---|---|
| 6,358,996 B1 * | 3/2002 | Alexander et al. .......... 514/449 |
| 6,440,705 B1 * | 8/2002 | Stanton et al. ............. 435/91.2 |
| 6,824,981 B2 * | 11/2004 | Chait et al. .................... 435/6 |
| 2003/0077616 A1 * | 4/2003 | Lomas .......................... 435/6 |
| 2003/0175844 A1 * | 9/2003 | Nadler et al. ................. 435/23 |
| 2004/0119010 A1 * | 6/2004 | Perryman et al. ........... 250/281 |
| 2005/0019223 A1 * | 1/2005 | Platt et al. ................... 422/100 |
| 2005/0042713 A1 * | 2/2005 | Thompson et al. ........ 435/68.1 |
| 2005/0112635 A1 * | 5/2005 | Gentle et al. .................. 435/6 |
| 2005/0224710 A1 * | 10/2005 | Matsuo et al. .............. 250/288 |
| 2005/0274884 A1 * | 12/2005 | Otake et al. ................ 250/282 |
| 2005/0277131 A1 * | 12/2005 | Jaffrey ........................... 435/6 |
| 2005/0282289 A1 * | 12/2005 | Ookubo et al. ............. 436/173 |

FOREIGN PATENT DOCUMENTS

| | | |
|---|---|---|
| JP | 3345401 | 8/2002 |
| JP | 2003-107066 | 4/2003 |

* cited by examiner

*Primary Examiner*—Jack Berman
*Assistant Examiner*—Bernard Souw
(74) *Attorney, Agent, or Firm*—Mattingly, Stanger, Malur & Brundidge, P.C.

(57) ABSTRACT

In a method of measuring by a tandem mass spectrometer a sample labeled with an isotope, measuring throughput is improved. In a technique in which tandem mass spectrometer is used to analyze a sample labeled with an isotope, spectra obtained by a first-stage measurement ($MS^1$) are analyzed during a measuring session in a realtime fashion to determine ions to be used in second-stage and subsequent dissociation• spectral measurement (MS2).

10 Claims, 6 Drawing Sheets

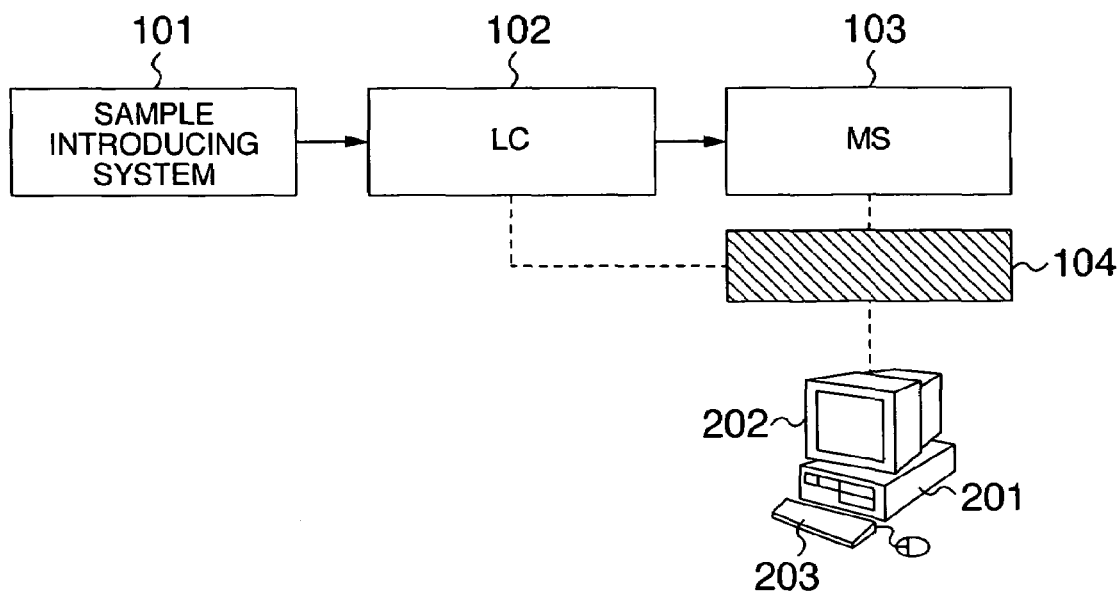
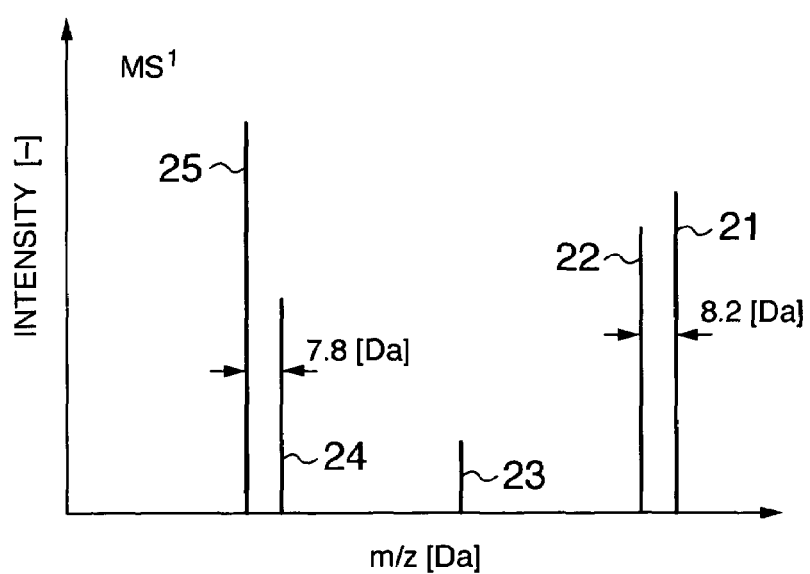

FIG. 5

| HOME | DATA BASE | LC/MS Config | Search Config |

// LC retention time; 1810 [s]

// Selected MS1 peak : m/z = 1146.6 (with reagent)

// Selected MS1 P1/P2 ratio < 0.70

// Search result (searching time 30[s])

| Rank | amino acid sequence(s) |
|---|---|
| 1 | KISNCDIK |
| 2 | ------------------- |
| 3 | ------------------- |
| 4 | ------------------- |

Protein(s): lipoprotein (Haemophilus influenzae Rd)...[more]

FIG. 7

| HOME | DATA BASE | LC/MS Config | Search Config |

SELECT PEAK JUDGING EXPRESSION

51 ☑ P1/P2 > [ 0.7 ] ~53
  (52)

54 ~[AND/OR] ☐ P1/P2 < [   ]

[AND/OR] ☐ P1×P2 < [   ]

[AND/OR] ☐ P1×P2 > [   ]

[AND/OR] ☐ P1−P2 > [   ]

[AND/OR] ☐ P1−P2 < [   ]

[AND/OR] ☐ [          ]  [EXECUTE]
                    ~59

MASS SPECTROMETRY AND MASS SPECTROMETRY SYSTEM

BACKGROUND OF THE INVENTION

The present invention relates to mass spectrometry and a mass spectrometry system, and in particular, to a mass spectrometer and a system for analyzing a mass spectrum in which biopolymeric substances such as protein, polypeptide, sugar, and nucleic acid are identified and are quantitatively determined with high precision and high throughput.

As protein identifying an determining methods utilizing a mass spectrometer (MS), a technique using isotope labeling has recently attracted attention. According to the technique, samples including a first sample and a second sample are obtained respectively from two test bodies, i.e., a first test body and a second test body. The first sample is bonded or combined with a "light reagent" and the second sample is combined with a "heavy reagent". The heavy and light reagents are equal in chemical structure. However, these reagents differ in the mass number from each other and hence are different in the molecular weight from each other.

When the first and second samples are mixed with each other and the mixture is measured by a mass spectrometer, there appear a pair of peaks apart from each other by difference ($\Delta m$) between the molecular weight values. If the first and second protein samples are attained respectively from the same test body and the samples are substantially equal in density and quantity to each other, the two peaks associated with the respective samples have substantially the same intensity. However, if a first sample is obtained from a sick test body and a second sample is attained from a healthy test body, there possibly appear a pair of peaks having mutually different peak intensity depending on cases.

By analyzing such peaks, it is possible to determine protein as a marker of a disease. The peak analysis is also expected to facilitate clarification of various protein functions.

The techniques using isotope labeling have been described in many articles, for example, JP-A-2003-107066 and Japanese Patent No. 3345401. The articles describe a method in which a reagent marked by an isotope is added to a measuring sample and the sample is analyzed by a tandem mass spectrometer capable of achieving multistage dissociation and measurement. There is also described a method in which by uses of an intensity ratio of the peak pair detected through a first-stage measurement (to be abbreviated as $MS^1$ hereinbelow), a second-stage measurement (to be abbreviated as $MS^2$ hereinbelow) is conducted to determine a protein array.

Description will now be given of a problem in the prior art. The tandem mass spectrometer can achieve multistage dissociation and measurement through one measuring session. Ordinarily, from peaks measured by $MS^1$, peaks required to identify an amino acid array are selected to conduct $MS^2$. By achieving database retrieval, an amino acid array corresponding to the $MS^2$ spectrum measured by $MS^2$ is determined. According to the measuring apparatus of the present stage of art, if the mass number associated with the "necessary peak" is known, a peak to be selected by $MS^1$ can be registered to the apparatus. Therefore, the dissociation and measurement up to $MS^2$ can be automatically carried out through one session.

If the mass number is unknown, $MS^1$ is first conducted to select a peak for $MS^2$. That is, the $MS^2$ spectrum is acquired through measurement in the second session. In an ordinary case, a liquid chromatograph (to be abbreviated as LC hereinbelow) is installed in a stage preceding the mass spectrometer. Constituent elements or components flown from the LC are used as a sample for the mass spectrometer. In the separation by the LC, a period of time of several seconds is required to obtain the elements to be measured depending on cases. The elements flow from a column of the LC for about ten seconds to 20 seconds. Therefore, if it is not possible that the $MS^1$ results are analyzed and the peak obtained by $MS^2$ is judged within the period of about ten seconds to 20 seconds, the time-consuming separation is required to be conducted by the LC. Additionally, since it is likely that composition of the constituent elements for the measurement vary between when the flow of the elements is started and when the flow thereof is stopped. Consequently, the peak thus measured is favorably selected within a period of time from about 0.1 second to one second.

In conjunction with the conventional method, description has not been given of a system in which the $MS^1$ spectrum is analyzed and a peak to be measured by $MS^2$ in such a short period of time, i.e., from about ten seconds to about 20 seconds. Therefore, in the method of prior art, for a sample for which a relationship between a mass number and occurrence of a peak pair having intensity ratio difference is known, an amino acid array of protein can be identified through at least one measurement session. However, for a sample for which the relationship is unknown, at least two measurement sessions are required to identify an amino acid array of protein. Since the throughput of LC is slow in general (about several hours), when the number of measurement sessions increases, the throughput including the identification of an amino acid array is considerably reduced. It can be considered that a need for rapid identification and quantitative determination increases in the future for, for example, application thereof to a diagnosis and medical treatment. This requires to remove any factors which lower the throughput.

SUMMARY OF THE INVENTION

To solve the problems above, the present invention provides a technique and associated devices and methods as below.

According to the present invention, there is provided a mass spectrometry including the steps of preparing a sample including a plurality of test bodies respectively labeled with reagents having mutually different molecular weights, separating constituent elements from the sample by chromatography, conducting a mass spectrometric analysis for the constituent elements by a tandem mass spectrometer capable of multistage dissociation and measurement, analyzing a result of the mass spectrometric analysis in a realtime fashion, and using in a realtime fashion a result of the analysis of at least one test body for a mass spectrometric analysis of other test bodies.

According to the present invention, there is provided a mass spectrometry system including a chromatograph for developing a sample including a plurality of test bodies respectively labeled with a plurality of isotope reagents, a tandem mass spectrometer connected to the chromatograph, the spectrometer being capable of conducting multistage dissociation and measurement; a unit for placing or moving the sample in an analysis area of the tandem mass spectrometer, an information processor for analyzing in a realtime fashion a result of the mass spectrometric analysis by the spectrometer, a controller for controlling the chromatograph and the tandem mass spectrometer, and an input/ output device for inputting necessary information to the controller and/or outputting necessary information from the controller.

In the description above, the chromatograph may be a liquid or gas chromatography apparatus. Realtime data analysis as well as changes and modifications of a mass spectrometry condition according to the data analysis are favorably achieved within at most one second, particularly favorably, within 0.1 second.

In accordance with the present invention, the identification and quantitative determination of biopolymer can be conducted with high throughput using a tandem mass spectrometer.

Other objects, features and advantages of the invention will become apparent from the following description of the embodiments of the invention taken in conjunction with the accompanying drawings.

BRIEF DESCRIPTION OF THE DRAWINGS

FIG. 1 is a block diagram schematically showing a first embodiment of a mass spectrometry system of the present invention.

FIG. 3 is a spectral graph obtained through $MS^1$ using mass spectrometry in an embodiment of the present invention.

FIG. 5 is a diagram showing an example of a display screen image in an embodiment of a mass spectrometry system of the present invention.

FIG. 7 is a diagram showing an example of a display screen image to select a judging expression in an embodiment of a mass spectrometry system of the present invention.

DESCRIPTION OF THE EMBODIMENTS

Figure 2:
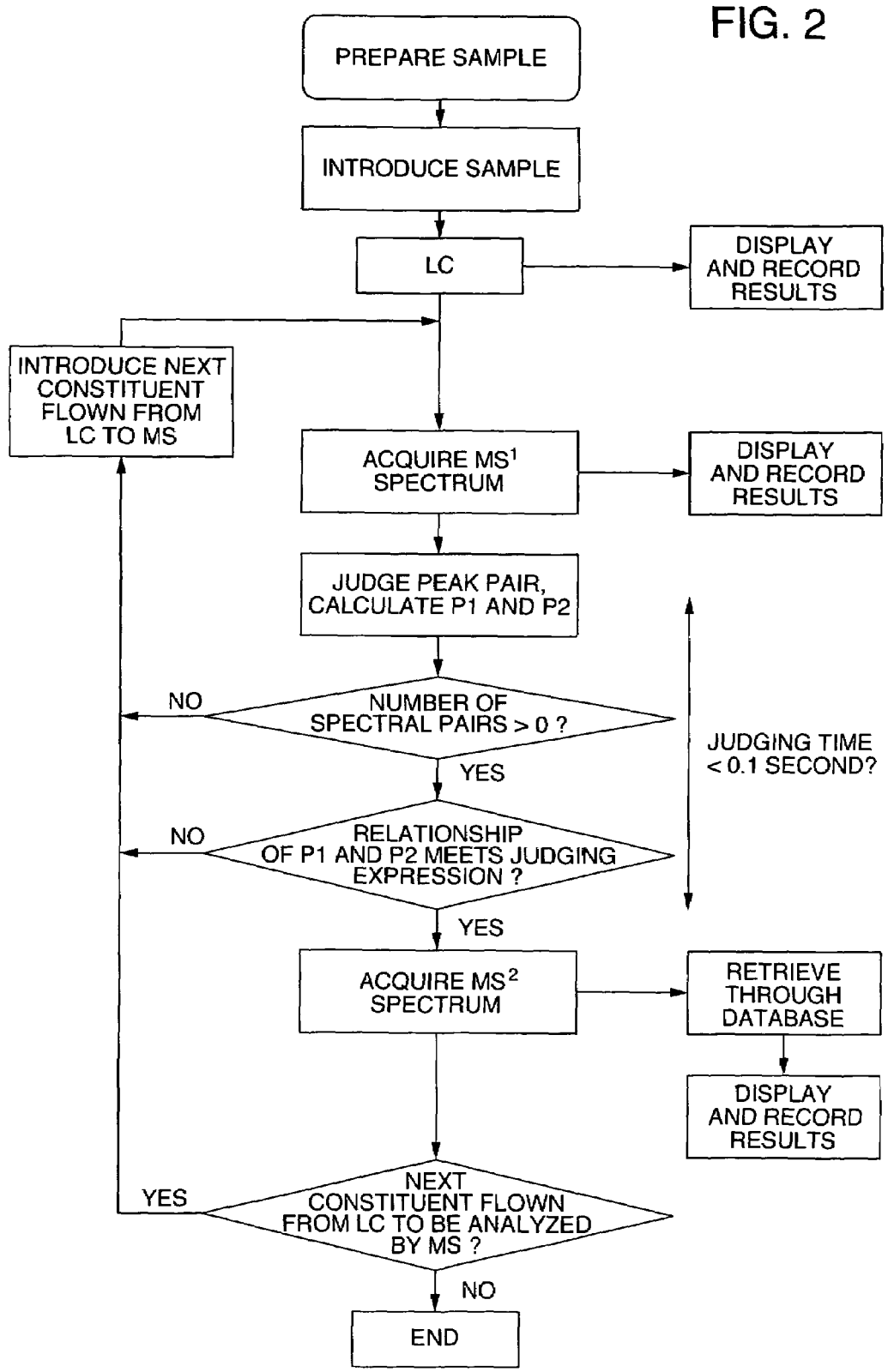
FIG. 2 is a flowchart to explain a mass spectrometry used in an embodiment of the present invention.
Figure 4:
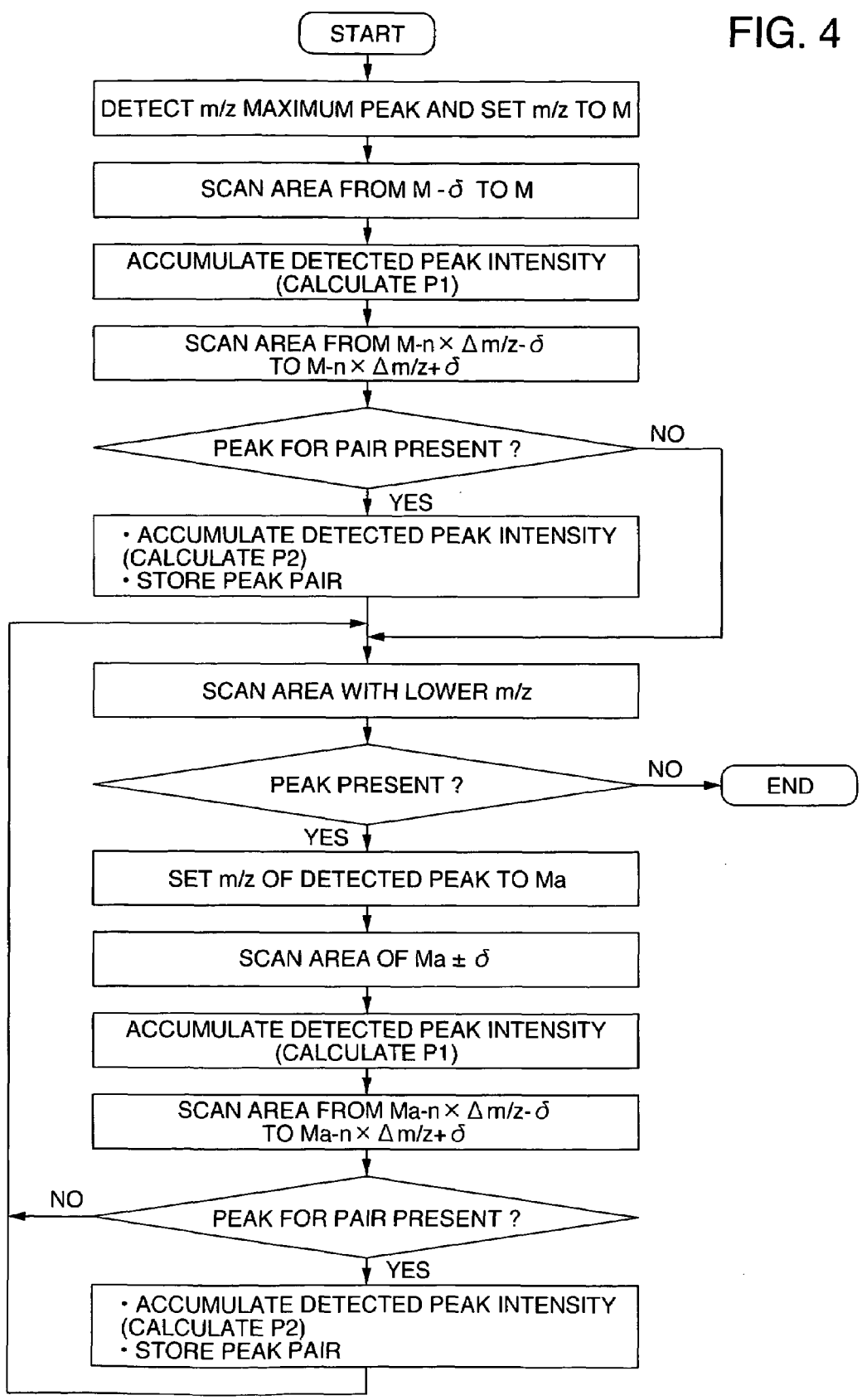
FIG. 4 is a flowchart showing a spectral pairing procedure in an embodiment of a mass spectrometry system of the present invention.

First, description will be given of an outline of a configuration in which the present invention is employed. According to the present invention, there is provided mass spectrometry and a mass spectrometry system in which a sample prepared by mixing a plurality of test bodies respectively labeled by reagents different in molecular weight from each other is measured by a tandem mass spectrometer. The system includes a tandem mass spectrometer capable of at least multistage dissociation and measurement, an information processor, and an input/output device. Therefore, a sample marked with an isotope can be identified and quantitatively determined at a high speed.

Preferably, according to the problem removing technique, there are provided a mass spectrometry and a mass spectrometry system in which an information processor analyzes in a realtime fashion a result of spectral measurement in a first-stage of the measurement by the tandem mass spectrometer capable of conducting a multistage dissociation and measurement. On the basis of a result of the analysis, ions for dissociation in second-stage and subsequent-stage measurement are selected in a realtime fashion.

In an ordinary tandem MS, peaks necessary to identify a sample are determined by $MS^1$, and structure of an object of measurement is clarified using spectra obtained by $MS^2$ or subsequent dissociation and measurement ($MS^n$, n>2). If peaks necessary for the measurement are known in advance, $MS^2$ (or, $MS^n$, n>2) can be conducted through one session using functions of the tandem MS. However, if such peaks are unknown, after analyzing $MS^1$ spectra, it is required to additionally conduct one measurement session. On the other hand, according to the present invention, peaks to be measured are extracted from $MS^1$ spectra during the measuring session in a realtime fashion to thereby conduct $MS^2$. As a result, even for an unknown sample, the analysis, identification, and quantitative determination thereof can be achieved through at least one measuring session, and hence throughput of measurement is remarkably increased.

Preferably, according to the problem removing technique, there are provided a mass spectrometry and a mass spectrometry system in which the isotope reagents for the labeling include two isotope reagents which are equal in molecular weight to each other and which are different in chemical structure from each other and the sample is a mixture including two test bodies labeled by the isotope reagents. As a result, samples labeled by two isotopes can be compared with each other and can be quantitatively determined at a high speed.

Preferably, according to the problem removing technique, there are provided a mass spectrometry and a mass spectrometry system. The method includes the steps of assuming that molecular weight difference between the two isotope reagents is $\Delta m$, extracting from spectra obtained through first-stage measurement a pair of peaks apart from each other by $n \times \Delta m$, where z is electric charge of an ion and n is a positive integer, and selecting, on the basis of a mutual relationship between spectral intensity of an extracted peak pair, a peak to be measured in second-stage and subsequent-stage measurement. As a result, a pair of peaks can be selected at a high speed.

Preferably, according to the problem removing technique, there are provided a mass spectrometry and a mass spectrometry system. The method includes the steps of assuming that the mass spectrometer has a mass number measuring error indicated by $\delta$, and treating, as pairs of peaks, all peaks in a range of $\pm\delta$ of a value m/z of a peak in consideration and peaks in a range from (a mass number of the peak in consideration$-n \times \Delta m/z + \delta$) to (the mass number of the peak in consideration$-n \times \Delta m/z - \delta$). It is therefore possible to conduct the analysis in consideration of a mass spectrometric error of a mass spectrometer.

Preferably, according to the problem removing technique, there is provided a mass spectrometry system in which the peak pair extraction utilizes the steps of starting extraction of a pair of peaks beginning at a peak selected from spectra measured in the peak pair extraction, the peak having a maximum value of m/z, and extracting thereby a pair of peaks in a descending m/z order.

Preferably, according to the problem removing technique, there is provided a mass spectrometry system which uses the steps of assuming in the peak pairs that intensity of a peak labeled by an isotope having a large mass number is P1, intensity of a peak labeled by an isotope having a small mass number is P2, and r takes a value set by a measuring operator, wherein a piece of a pair of peaks or both thereof satisfying a judging expression P1/P2>r or P1/P2<r is or are dissociated in second-stage and subsequent-stage measurement. Therefore, the peak judgment can be mechanically conducted using a judging expression, and hence peaks to be measured in second-stage and subsequent-stage measurement can be determined by an information processor at a high speed.

Preferably, according to the problem removing technique, there are provided a mass spectrometry and a mass spectrometry system. The method includes the steps of accumulating all intensity values of peaks in a range of ±δ of a value m/z of a peak in consideration labeled by an isotope having a large mass number and thereby obtaining P1 as a result of the accumulation, wherein accumulating all intensity values of peaks in a range of ±δ of a value m/z of a peak in consideration labeled by an isotope having a small mass number and thereby obtaining P2 as a result of the accumulation. The analysis can be therefore conducted in consideration of a mass spectrometric error of MS.

Preferably, according to the problem removing technique, there are provided a mass spectrometry and a mass spectrometry system. The method includes the steps of assuming that the judging expression is P1−P2>r2 or P1−P2<r2 and r2 takes a value set by the measuring operator, wherein a piece of a pair of peaks or both thereof satisfying the judging expression is or are dissociated in second-stage and subsequent-stage measurement. Therefore, the peak judgment can be mechanically conducted using a judging expression, and hence peaks to be measured in second-stage and subsequent-stage measurement can be determined by an information processor at a high speed.

Preferably, according to the problem removing technique, there are provided a mass spectrometry and a mass spectrometry system. The method includes the steps of assuming the judging expression is P1×P2>r3 or P1'P2<r3 and r3 takes a value set by the measuring operator, wherein a piece of a pair of peaks or both thereof satisfying the judging expression is or are dissociated in second-stage and subsequent-stage measurement. Therefore, the peak judgment can be mechanically conducted using a judging expression, and hence peaks to be measured in second-stage and subsequent-stage measurement can be determined by an information processor at a high speed.

Preferably, according to the problem removing technique, there are provided a mass spectrometry and a mass spectrometry system. The method includes the steps of assuming the judging expression is r4>P1/P2>r5 and r4 and r5 take values set by the measuring operator, wherein a piece of a pair of peaks or both thereof satisfying the judging expression is or are dissociated in second-stage and subsequent-stage measurement. Therefore, the peak judgment can be mechanically conducted using a judging expression, and hence peaks to be measured in second-stage and subsequent-stage measurement can be determined by an information processor at a high speed.

Preferably, according to the problem removing technique, there is provided a mass spectrometry system. The method utilizes the steps of arbitrarily setting the judging expression by the measuring operator, wherein a piece of a pair of peaks or both thereof satisfying the judging expression is or are dissociated in second-stage and subsequent-stage measurement. Therefore, the peak judgment can be mechanically conducted using a judging expression, and hence peaks to be measured in second-stage and subsequent-stage measurement can be determined by an information processor at a high speed.

Preferably, according to the problem removing technique, there is provided a mass spectrometry system in which the test body as an object of measurement is protein, peptide obtained by decomposing protein, chemically modified peptide, sugar, or nucleic acid. It is therefore possible to conduct the identification and the quantitative determination of general biopolymer.

Preferably, according to the problem removing technique, there are provided a mass spectrometry and a mass spectrometry system. The method includes the steps of using, when labeling protein, peptide obtained by decomposing protein, or chemically modified peptide, an isotope reagent which specifically bonds with cystine or tryptophane contained in the protein or peptide obtained by decomposing the protein, or the chemically modified peptide.

Therefore, by using a reagent which specifically bonds with an amino acid residue having a low existing quantity, the spectral analysis can be simplified, and throughput and identifying precision can be increased. Additionally, there are provided a mass spectrometry and a mass spectrometry system. In the mass spectrometry, the isotope reagent is an isotope of hydrogen, an isotope of oxygen, an isotope of carbon, an isotope of nitrogen, an isotope of phosphorus, or a combination thereof. As a result, according to an object of measurement, an optimal reagent labeled by an isotope can be selected.

Preferably, there are provided a mass spectrometry and a mass spectrometry system. The mass spectrometry system includes an information processor for conducting database retrieval and either one of or both of a network connecting device and a data storage. This increases the database retrieval speed, and an object of measurement can be identified and quantitatively determined during the measurement in a realtime fashion.

Description will now be given in detail of an embodiment of the present invention.

First Embodiment

Referring to FIGS. 1 to 5, description will be given of an embodiment of a mass spectrometry system according to the present invention. The system shown in FIG. 1 includes a sample introducing system 101, a liquid chromatograph (LC) 102, a tandem mass spectrometer (MS) 103, a control unit 104, a computer 201, a display 202 as an output device, a keyboard 203 as an input device, and signal lines connecting the constituent components to each other. The mass spectrometer 103 is a device of ion trap type in which ionization is conducted in an electro-spray ionization method. Under a utilization condition of the embodiment, a mass measurement error of the mass spectrometer δ 103 is about 0.5 Da, where Da is an atomic weight unit, i.e., one Da=one atomic weight unit.

The system of the embodiment shown in FIG. 1 operates according to a flowchart of FIG. 2. Next, the system operation of the embodiment will be described. Assume that protein identification and quantitative determination are conducted for two test bodies A and B. The test bodies A and B are extracted from the same tissue of animals of the same kind and are equal in density and quantity to each other. However, the individual items A and B are separated from each other. The object of the analysis is to determine difference in protein manifestation and identification of the protein according to the individual items.

The test bodies A and B are labeled by two isotope reagents a and b. The reagents a and b are equal in chemical composition to each other, but differ in the number of carbon isotope ($C^{12}$ and $C^{13}$) from each other. While the constitution of the reagent a includes eight $C^{13}$, the constitution of the reagent b includes only $C^{12}$. The molecular weight of reagent a is more than that of the reagent b by eight. The reagents a and b have a property to bond or couple with only cysteine residues in protein.

The test bodies A and B are decomposed by a digestive enzyme. Samples of an equal quantity derived from the decomposition of the test bodies A and B are mixed with each other and the mixed sample is set to the sample introducing system 101. The sample from the system 101 is separated by the liquid chromatograph 102 to be fed to the tandem mass spectrometer 103. The controller 104 controls operation of the units 102 and 103. The computer 201 controls the controller 104. The computer 201 issues an indication to the controller 104 according to a measuring condition beforehand designated by the measuring operator from the keyboard 203. The computer 201 records $MS^1$ spectral data obtained from the chromatograph 102 and the mass spectrometer 103.

Next, the obtained $MS^1$ spectral data is analyzed to judge a peak pair associated with the test bodies A and B. If peptide in the constitution from the liquid chromatograph includes cysteine residue, two peaks appear at positions apart by m/z=8 from each other, and hence the peak pair can be judged. It is assumed in this situation that the peptide includes only one cysteine residue, that is, n=1.

The operation will be described by referring to FIG. 3. FIG. 3 is a graph schematically showing peaks derived from the test body A and those of the test body B in the $MS^1$ spectral data. It has been known as a result of a spectral analysis that the peaks of FIG. 3 are derived from ions with valence=1 (z=1). The spectral graph of FIG. 3 includes main peaks 21 to 25. The distance between the peaks 21 and 22 is 8.2 Da and that between the peaks 24 and 25 is 7.8 Da.

The computer 210 carries out spectral pairing on the basis of the mass measurement error $\delta$ of the spectrometer 103 and the mass difference $\Delta m$ between the reagents a and b. The pairing is generally conducted in a procedure indicated by a flowchart of FIG. 4. Referring now to the flowchart of FIG. 4, description will be given of a procedure to extract a peak pair from the spectral data shown in FIG. 3. Unless otherwise designated by the measuring operator, the pairing is conducted beginning at a highest peak of m/z. In the case of FIG. 3, the operation is initiated beginning at the peak 21.

The mass number of the peak 21 is 1510.1. First, a search is made for peaks in a range of $-\delta$ from the peak 21, that is, for m/z in a range from 1509.6 to 1510.1. Obtained peaks are recorded as peaks belonging to the peak 21. Intensity of each peak belonging to the peak 21 is accumulated and the accumulated result is recorded as a value of P1 of the peak 21. To detect a peak as another piece of the pair, a search is made for peaks in an area ranging from $1510.1-n\times\Delta m/z-\delta$ to $1510.1-n\times\Delta m/z+\delta$.

Since n=1, $\Delta m=8$, $\delta=0.5$, and z=1; a search is made for peaks in a range of mass weight from 1501.6 to 1502.6. In FIG. 3, the peak 22 meets the condition, and hence the peaks 21 and 22 are registered as a peak pair. Intensity of each peak belonging to the peak 22 is accumulated and the accumulated result is stored as P2 of the peak 22. By further widening the area toward a smaller value of m/z, the peak 23 is detected. Since no peak near the peak 23 can be paired therewith, the search is made in an area by widening the area toward a smaller value of m/z without conducting the pairing of the peak 23. The next detected peak is the peak 24 (m/z=1146.6).

Assume that peaks in the area expressed as $m/Z\pm\delta$ of the peak 24 belong to the peak 24. As in the case of the peak 21, intensity of each peak belonging to the peak 24 is accumulated and the accumulated result is stored as P1 of the peak 24. Next, a search is made for peaks in an area from $1146.6-n\times\Delta m/z-\delta$ to $1146.6-n\times\Delta m/z+\delta$. This results in detection of the peak 25, and hence the peaks 24 and 25 are registered as a peak pair. Intensity of each peak belonging to the peak 25 is accumulated and the accumulated result is stored as P2 of the peak 25. If any peak exists in an area for a further lower value of m/z relative to an m/z value of the peak 25, the search is continuously carried out. Since there exists no peak for m/z less than an m/z value associated with the peak 25 in the embodiment, the search is terminated at this point. If no peak pair is detected by the termination of the search, the measurement of the $MS^2$ spectrum is not carried out. After next constituent has flown from the chromatograph, acquisition of the $MS^1$ spectrum is carried out again for the constitution.

To avoid influence from background noise in the operation, it is favorable to beforehand set a threshold value such that a peak with intensity equal to or less than the threshold value is not used for the peak pair search.

From the peak pairs obtained as above, the system selects an $MS^1$ peak to be measured according to a relationship between the intensity P1 of the peak derived from the test body A and the intensity P2 of the peak derived from the test body B. Assume that the judging expression is P1/P2<r and the judging value r=0.7. Judgment is conducted for all peak pairs to determine whether or not the expression is satisfied. In the embodiment, P1/P2=1.1 for the peaks 21 and 22 and hence the peaks 21 and 22 do not satisfy the judging expression. For the peaks 24 and 25, P1/P2=0.6 and the expression is satisfied. Therefore, the peaks 24 and 25 are determined as peaks for the $MS^2$ measurement, and hence an m/z value is recorded for each of the peaks 24 and 25. If a plurality of peaks are determined, an m/z value is recorded for each thereof. A period time from when the result of the $MS^2$ measurement is obtained to when the peaks are determined is at most 0.1 second even when a general personal computer is used.

Next, the $MS^2$ measurement is conducted for the selected peaks. Since two selected peaks exist for each peak pair, the $MS^2$ measurement is conducted for either one or both of the peaks. In the embodiment, the $MS^2$ measurement is conducted for only the peak labeled by a light isotope, i.e., the peak 25.

Using the information obtained through the $MS^2$ measurement, a retrieval operation is conducted through a mass spectral database included in the computer 201 to extract therefrom an amino acid array conforming to the information. The retrieval result and other data items are stored in a hard disk of the computer 201 and is presented on the display 202 thereof. FIG. 5 shows an example of information items displayed on the display 202. The example includes the following items.

(1) LC retention time of peak measured by MS
(2) Value of selected $MS^1$ m/z value
(3) Value of selected $MS^1$ P1/P2 value
(4) Database search result: Candidate amino acid arrays displayed in an order of rank
(5) Names of protein including candidate amino acid arrays of (4)

The measurement operator can arbitrarily display information items such as a measuring condition and a database search condition on the display 202.

The database search possibly requires a period of time ranging from several minutes to several hours depending on cases. Therefore, the search and the measurement are concurrently carried out. This means that it does not usually occur that after a search operation is finished, a subsequent measuring operation is conducted. The tandem MS 103 conducts the $MS^2$ measurement for all selected peaks (part of the selected peaks when the operator designates a desired mode for measurement). After subsequent constitution flows from the LC, the MS 103 starts again $MS^1$ spectral measurement.

According to the embodiment, of the proteins included in the test bodies A and B, proteins having difference in occurrence between individual bodies or items can be particularly identified. Also, since the operation including the $MS^1$ measurement, the $MS^2$ measurement, and the database retrieval can be achieved through one session of measurement, the identification and the quantitative determination of protein can be carried out with high throughput.

Second Embodiment

Figure 6:
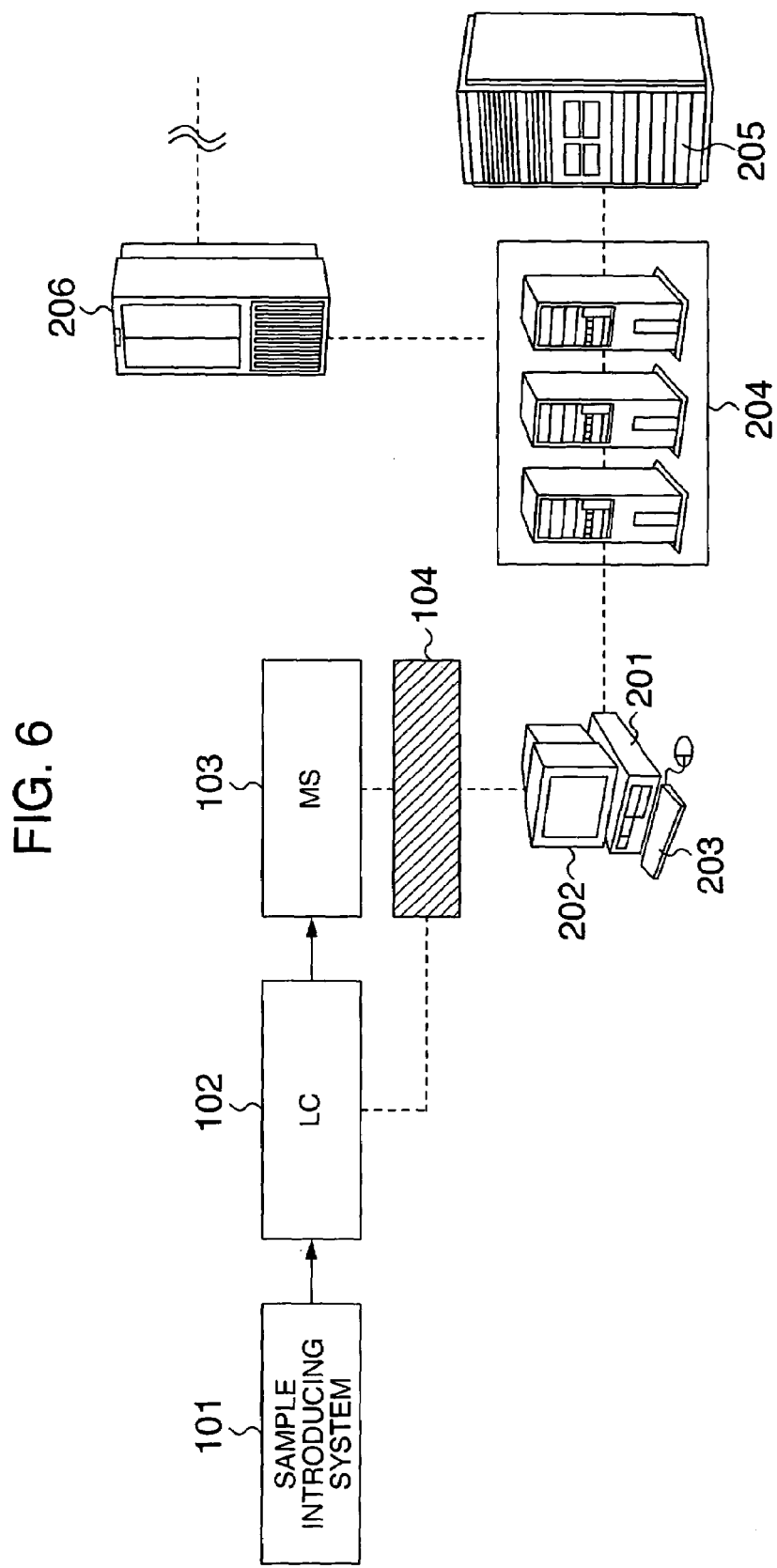
FIG. 6 is a schematic block diagram showing a second embodiment of a mass spectrometry system of the present invention.

Referring to FIG. 6, description will be given of an embodiment of a mass spectrometry system according to the present invention. The system shown in FIG. 6 is implemented by connecting a cluster computer 204, a data storage 205, and a network server 206 to the system of FIG. 1.

The system of FIG. 6 is basically equal in operation to that of FIG. 1, but there exists difference therebetween as below. The spectral data obtained through the $MS^2$ measurement is processed by the cluster computer 204, not by the computer 201. The database is not included in the computer 201, but is stored in a high-speed data storage 205 having large storage capacity. Thanks to the network server 206, a database on an external network can be used.

Use of the system of the embodiment makes it possible to conduct high-speed database retrieval, and hence the period of time from the $MS^2$ measurement to the amino acid array determination can be remarkably reduced. When the cluster computer 204 has sufficient capacity for operation, the $MS^2$ measurement and the amino acid array determination can be achieved almost at the same time (realtime determination of the array).

Third Embodiment

Although the first embodiment employs P1/P2<r as the judging expression, there may be used judging expressions as follows.

(1) P1/P2>r
(2) P1−P2>r2 or P1−P2<r2
(3) P1×P2>r3 or P1×P2<r3
(4) r4>P1/P2>r5

The condition of (1) is used when P1/P2>r obviously holds. The condition of (2) is used when there exists spectral intensity difference. The condition of (3) is used when a spectral intensity product is significant. The condition of (4) is used to confirm whether or not proteins contained in two test bodies A and B are associated with peaks actually derived from the same protein.

Using the judging expressions described above, the identification and the quantitative determination of proteins can be carried out with high throughput through one session of measurement as in the first embodiment. The similar advantage can also be obtained by using a combination of the above judging expressions.

Fourth Embodiment

Description will now be given of a method of setting a combination of judging expressions or a particular judging expression in the embodiment described above. In the fourth embodiment, before the measurement is started or before the $MS^2$ measurement is executed after the measurement is started, a condition is set for the judging expression by the computer 201, the display 202, and the keyboard 203 shown in FIG. 1. When the setting of a judging expression is designated, an input screen image is presented on the display 202 as shown in FIG. 7. The input screen image includes a check box 51, a judging expression 52, a judging value input field 53, an AND/OR setting field 54, and a particular judging expression input field 59.

Description will now be given of a method of setting a judging expression using the interface. The measuring operator checks a judging expression check box 51 for a desired judging expression and then inputs a judging value in an associated input field 53. When a plurality of judging expressions are desired, the AND/OR setting field 54 is used. To set conditions for judging expressions, if both conditions are to be satisfied, the operator selects AND. If either one thereof is to be satisfied, the operator selects OR. When it is desired to employ a particular judging expression, the operator inputs the judging expression in the field 59. After the input items are completely set in the screen, the operator depresses Decision or Execute button to thereby actually set the judging expression. If the designated judging expressions conflict with each other, a warning message is displayed. The operator conducts again an input operation to set a judging expression.

According to the embodiment, it is possible to combine a plurality of judging expressions or to designate a particular judging expression. Using the judging expressions described above, the identification and the quantitative determination can be carried out with high throughput as in the above embodiments.

Fifth Embodiment

In the above embodiments, the test bodies A and B may be protein, chemically modified peptide, sugar, or nucleic acid. When the test bodies are sugar, there is used an isotope reagent which specifically bonds or combines with a particular monosacharide. When the test bodies are nucleic acid, there is used an isotope reagent which specifically bonds with a particular base or a particular base array.

As in the embodiments described above, even when the samples to be measured are general biopolymer, structure thereof can be identified and quantity thereof can be determined with high throughput through one measuring session.

Sixth Embodiment

For protein, peptide obtained by decomposing protein, or chemically modified peptide in the above embodiment, it is also possible to use an isotope reagent which specifically bonds with tryptophane contained in an amino acid array. Since tryptophane has a lower-most existing ratio in protein derived from a living body (existing ratio=1.18%; Swissprot protein knowledge database), the spectral analysis is advantageously simplified.

Figure 8:
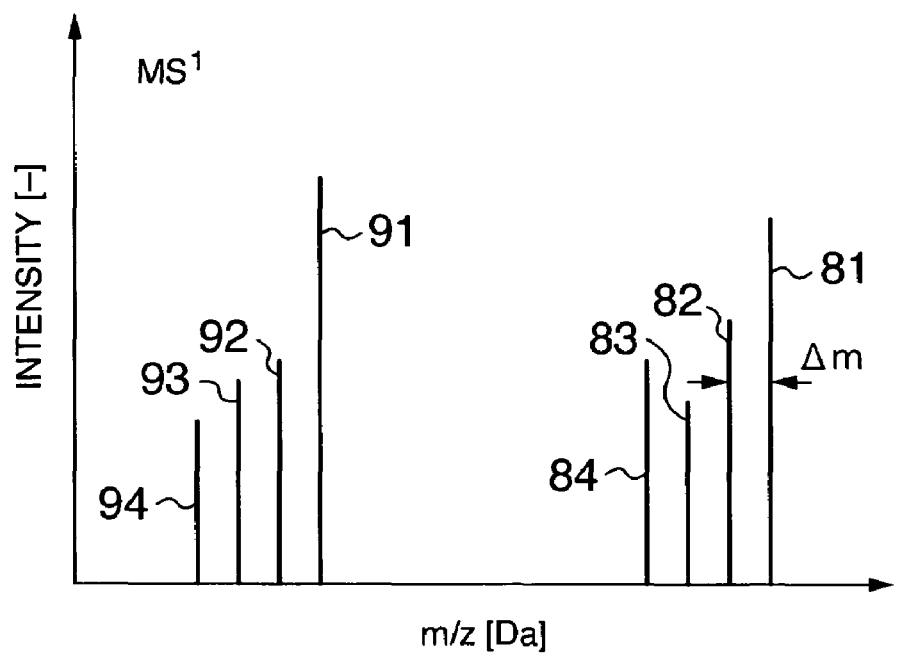
FIG. 8 is a spectral graph obtained using mass spectrometry in an embodiment of the present invention in which spectral groups are separated from each other.
Figure 9:
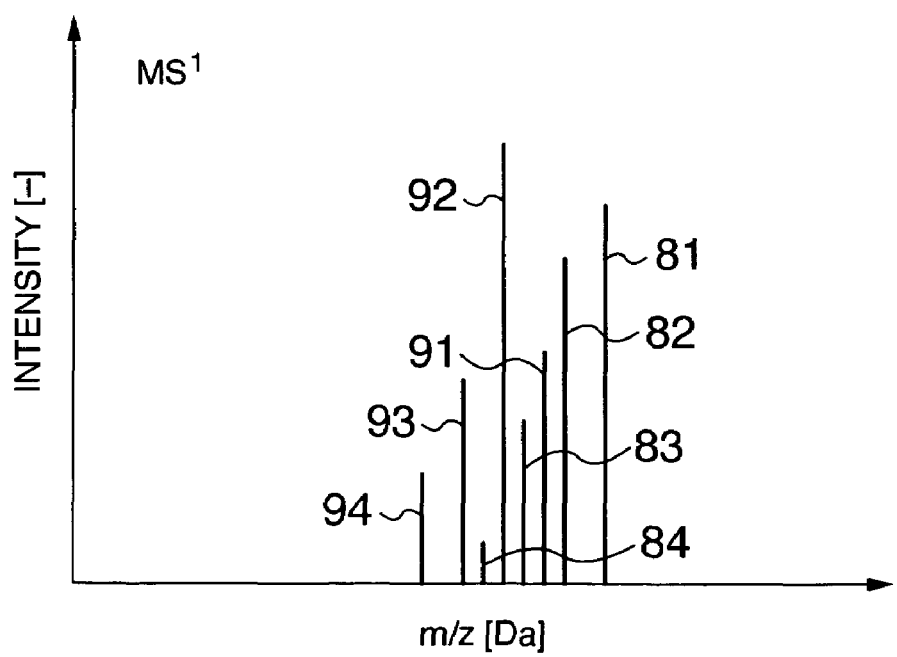
FIG. 9 is a spectral graph obtained using mass spectrometry in an embodiment of the present invention in which spectral groups overlap with each other.

The spectral analysis will be described by referring to FIGS. 8 and 9. FIG. 8 shows an example of a $MS^1$ spectral graph obtained using an isotope reagent which bonds with an amino acid residue having a high existing quantity. Peptide chains measured and presented in FIG. 8 include amino acid residues bonded with a plurality of isotope reagents. Therefore, while only one paired peak appears in the first embodiment, two or more peaks appear for a peak pair in the sixth embodiment. In FIG. 8, while peaks 81 to 83 and 91 to 93 are derived from the test body A of the first embodiment, peaks 84 and 94 are derived from the test body B.

To analyze the spectra of FIG. 8, it is required to extract peak pairs by setting the value of n to "3" in the first embodiment. When the group of peaks 81 to 84 overlaps with that of peaks 91 to 94 (FIG. 9), the spectral analysis becomes more difficult. There can be possibly obtained one peak, not a plurality of peaks, by use of a sufficiently highly reactive reagent. However, the value of m/z between the peaks associated respectively with the test bodies A and B is increased, and hence possibility of overlapping between a plurality of peak groups becomes higher. On the other hand, since tryptophne is a amino acid residue having a lowest existing ratio in bioprotein, it is highly possible that a plurality of isotope reagents bond wit one peptide compound.

This simplifies the spectral analysis and the identification and the quantitative determination of protein can be carried out with high throughput and high precision. Similarly, as compared with protein, cysteine has a next lowest existing ratio in bioprotein (existing ratio=1.6%; SwissProt Protein Knowledgedatabase). Therefore, the advantageous effect described above can also be expected. According to the sixth embodiment, the spectral analysis is simplified and hence the identification and the quantitative determination can be carried out with high throughput and high precision.

Seventh Embodiment

In the above embodiment, the general isotope reagent is a regent containing an isotope of carbon or hydrogen. In the seventh embodiment, the similar advantageous effect can be obtained by use of a reagent containing an isotope of oxygen, an isotope of carbon, an isotope of nitrogen, an isotope of phosphorus, or a reagent containing a combination thereof.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A mass spectrometry, comprising the steps of:
    preparing a sample including a plurality of test bodies respectively labeled with isotope reagents having mutually different molecular weights;
    separating constituent elements from the sample by chromatography;
    conducting a mass spectrometric analysis for the constituent elements by a tandem mass spectrometer capable of multistage dissociation and measurement;
    analyzing a result of the mass spectrometric analysis in a realtime fashion;
    using in a realtime fashion a result of the analysis of at least one test body for a mass spectrometric analysis of other test bodies;
    wherein:
    the isotope reagents for the labeling include two isotope reagents which are equal in chemical structure to each other and which are different in molecular weight from each other; and
    the sample is a mixture including two test bodies labeled by the isotope reagents.

2. A mass spectrometry according to claim 1, further comprising the steps of:
    assuming that molecular weight difference between the two isotope reagents is $\Delta m$;
    extracting from spectra obtained through first-stage measurement a pair of peaks apart from each other by $n \times \Delta m/z$, where z is electric charge of an ion and n is a positive integer; and
    selecting, on the basis of a mutual relationship between spectral intensity of an extracted peak pair, a peak to be measured in second-stage and subsequent-stage measurement.

3. A mass spectrometry according to claim 2, further comprising the steps of:
    assuming that the mass spectrometer has a mass number measuring error indicated by $\delta$; and
    treating, as pairs of peaks, all peaks in a range of $\pm\delta$ of a value m/z of a peak in consideration and peaks in a range from (a mass number of the peak in consideration$-n \times \Delta m/z+\delta$) to (the mass number of the peak in consideration$-n \times \Delta m/z-\delta$).

4. A mass spectrometry according to claim 3, further comprising the steps of:
    starting extraction of a pair of peaks beginning at a peak selected from spectra measured in the peak pair extraction, the peak having a maximum value of m/z, and extracting thereby a pair of peaks in a descending m/z order.

5. A mass spectrometry according to claim 2, further comprising the steps of:
    assuming in the peak pairs that intensity of a peak labeled by an isotope having a large mass number is P1, intensity of a peak labeled by an isotope having a small mass number is P2, and r takes a value set by a measuring operator, wherein
    a piece of a pair of peaks or both thereof satisfying a judging expression P1/P2>r or P1/P2>r is or are dissociated in second-stage and subsequent-stage measurement.

6. A mass spectrometry according to claim 5, further comprising the steps of:
    accumulating all intensity values of peaks in a range of $\pm\delta$ of a value m/z of a peak in consideration labeled by an isotope having a large mass number and thereby obtaining P1 as a result of the accumulation, wherein
    accumulating all intensity values of peaks in a range of $\pm\delta$ of a value m/z of a peak in consideration labeled by an isotope having a small mass number and thereby obtaining P2 as a result of the accumulation.

7. A mass spectrometry according to claim 5, further comprising the steps of:
    assuming that the judging expression is P1−P2>r2 or P1−P2<r2 and r2 takes a value set by the measuring operator, wherein
    a piece of a pair of peaks or both thereof satisfying the judging expression is or are dissociated in second-stage and subsequent-stage measurement.

8. A mass spectrometry according to claim 5, further comprising the steps of:
    assuming the judging expression is P1×P2>r3 or P1×P2<r3 and r3 takes a value set by the measuring operator, wherein
    a piece of a pair of peaks or both thereof satisfying the judging expression is or are dissociated in second-stage and subsequent-stage measurement.

9. A mass spectrometry according to claim 5, further comprising the steps of:
    assuming the judging expression is r4>P1/P2>r5 and r4 and r5 take values set by the measuring operator, wherein
    a piece of a pair of peaks or both thereof satisfying the judging expression is or are dissociated in second-stage and subsequent-stage measurement.

10. A mass spectrometry according to claim 5, further comprising the steps of:
    arbitrarily setting the judging expression by the measuring operator, wherein
    a piece of a pair of peaks or both thereof satisfying the judging expression is or are dissociated in second-stage and subsequent-stage measurement.

* * * * *